(12) United States Patent
Lin et al.

(10) Patent No.: US 7,456,272 B2
(45) Date of Patent: Nov. 25, 2008

(54) NEUROTOXINS WITH ENHANCED TARGET SPECIFICITY

(75) Inventors: Wei-Jen Lin, Cerritos, CA (US); Kei Roger Aoki, Coto de Caza, CA (US); Lance E. Steward, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/832,901

(22) Filed: Aug. 2, 2007

(65) Prior Publication Data

US 2007/0292920 A1 Dec. 20, 2007

Related U.S. Application Data

(62) Division of application No. 09/726,949, filed on Nov. 29, 2000, now Pat. No. 7,273,722.

(51) Int. Cl.
*C07H 21/04* (2006.01)
(52) U.S. Cl. ............... 536/23.7; 435/69.1; 435/69.7; 435/71.1; 435/71.2; 435/252.3; 435/252.33; 435/320.1; 536/23.4
(58) Field of Classification Search ............... None
See application file for complete search history.

(56) References Cited

U.S. PATENT DOCUMENTS

| | | | |
|---|---|---|---|
| 5,562,907 A | 10/1996 | Arnon | |
| 5,728,399 A | 3/1998 | Wu et al. | |
| 5,763,250 A | 6/1998 | Williams et al. | |
| 5,837,265 A | 11/1998 | Montel et al. | |
| 5,939,070 A | 8/1999 | Goodnough et al. | |
| 5,989,545 A | 11/1999 | Foster et al. | |
| 6,022,950 A | 2/2000 | Murphy | |
| 6,066,621 A | 5/2000 | Sela et al. | |
| 6,087,327 A | 7/2000 | Pearce et al. | |
| 6,113,946 A | 9/2000 | Szoka et al. | |
| 6,203,794 B1 * | 3/2001 | Dolly et al. | 424/184.1 |
| 6,221,355 B1 | 4/2001 | Dowdy | |
| 6,312,708 B1 | 11/2001 | Donovan | |
| 6,333,303 B1 | 12/2001 | Borgford | |
| 6,342,221 B1 | 1/2002 | Thorpe et al. | |
| 6,361,938 B1 | 3/2002 | O'Mahony et al. | |
| 6,383,775 B1 | 5/2002 | Duff et al. | |
| 6,395,513 B1 | 5/2002 | Foster et al. | |
| 6,416,959 B1 | 7/2002 | Giuliano | |
| 6,426,075 B1 | 7/2002 | Fitzgerald et al. | |
| 6,444,209 B1 | 9/2002 | Johnson et al. | |
| 6,461,617 B1 | 10/2002 | Shone et al. | |
| 6,670,147 B1 | 12/2003 | Heidtmann et al. | |
| 7,056,729 B2 * | 6/2006 | Donovan | 435/320.1 |
| 7,132,259 B1 * | 11/2006 | Dolly et al. | 435/69.1 |
| 7,262,291 B2 * | 8/2007 | Donovan | 536/23.7 |
| 7,273,722 B2 * | 9/2007 | Lin et al. | 435/69.1 |
| 2002/0045208 A1 | 4/2002 | Eck et al. | |
| 2002/0177545 A1 | 11/2002 | Donvan | |
| 2006/0099672 A1 * | 5/2006 | Dolly et al. | 435/68.1 |
| 2007/0259003 A1 * | 11/2007 | Donovan | 424/239.1 |
| 2007/0259401 A1 * | 11/2007 | Dolly et al. | 435/69.1 |
| 2008/0032930 A1 * | 2/2008 | Steward et al. | 514/12 |
| 2008/0096248 A1 * | 4/2008 | Steward et al. | 435/69.1 |

FOREIGN PATENT DOCUMENTS

| | | |
|---|---|---|
| WO | 95/32738 | 12/1995 |
| WO | 98/07864 | 2/1998 |
| WO | 98/20135 | 5/1998 |
| WO | 00/61768 | 10/2000 |
| WO | 01/14570 | 3/2001 |

OTHER PUBLICATIONS

Li Yan et al, "Expression and characterization of the heavy chain of tetanus toxin: Reconstitution of the fully-recombinant dichain protein in the active form", Journal of Biochemistry, vol. 125, No. 6, Jun. 1999, pp. 1200-1208.
Ashton Anthony et al, "Tetanus toxin inhibits neuroexocytosis even when its Zn-2+-dependent protease activity is removed", Journal of Biological Chemistry, vol. 270, No. 52, 1995, pp. 31386-31390.
Aravamudan et al, Journal of Neurobiology, vol. 54, pp. 417-438, 2003.
Bryant et al, The EMBO Journal, vol. 20, pp. 3380-3388, 2001.
Hayashi et al, Plant and Cell physiology (Japan), Sep. 2001, vol. 42-9, pp. 894-899.
Flaumenhaft, Arteriosclerosis, thrombosis and vascular biology, Jul. 1, 2003, vol. 23(7), pp. 1152-1160.
Ernst, Cellular Microbiology, vol. 2(5) pp. 379-386, 2000.
Borodic et al, "Pharmacology and Histology of the Therapeutic Application of Botulinum Toxin", In Therapy with Botulinum Toxin, pp. 119-157, 1994.
Chaddock et al, Infection and Immunity, vol. 68(5), pp. 2587-2593, May 2000.
Zhou et al, Biochemistry, vol. 34(46), pp. 15175-15181, 1995.
Aoki et al, Eur. J. Neurol., vol. 6 (suppl 4), pp. S3-S10, 1999.
Carter, Chapter 13, Site specific proteolysis of Fusion proteins, pp. 181-193, American Chemistry Society, In Protein Purification: From Molecular Mechanisms to Large Scale Processes.
Niemann et al, Trends in Cell Biology, vol. 4, pp. 179-185, 1994.
O'hara et al, FEBS, vol. 273(1-2), pp. 200-204, Oct. 1990.
Robinson et al, Journal of Biological Chemistry, vol. 250(18), pp. 7435-7442, Sep. 25, 1975.
Woody et al, Toxicon, vol. 27(10), pp. 1143-1150, 1989.
Yan et al, Biochemistry, Vo. 33(22), pp. 7014-7020, 1994.
Montecucco et al, Trends in biochemistry, vol. 18,, pp. 324-327, 1993.
Walker et al, Bio/Technology, vol. 12, pp. 601-605, Jun. 1994.

* cited by examiner

*Primary Examiner*—Mark Navarro
*Assistant Examiner*—Ginny Portner
(74) *Attorney, Agent, or Firm*—Dean G. Stathakis; Joel B. German; Martin A. Voet

(57) ABSTRACT

Modified neurotoxins that contain protease cleavage sites susceptible uniquely to proteases present in certain tissues are described. The toxins can be selectively activated by proteases in muscle or selectively inactivated by proteases in blood.

20 Claims, 3 Drawing Sheets

Fig. 1A.

```
  1  PFVNKQFNYK DPVNGVDIAY IKIPNVGQMQ PVKAFKIHNK IWVIPERDTF TNPEEGDLNP
 61  PPEAKQVPVS YYDSTYLSTD NEKDNYLKGV TKLFERIYST DLGRMLLTSI VRGIPFWGGS
121  TIDTELKVID TNCINVIQPD GSYRSEELNL VIIGPSADII QFECKSFGHE VLNLTRNGYG
181  STQYIRFSPD FTFGFEESLE VDTNPLLGAG KFATDPAVTL AHELIHAGHR LYGIAINPNR
241  VFKVNTNAYY EMSGLEVSFE ELRTFGGHDA KFIDSLQENE FRLYYNKFK DIASTLNKAK
301  SIVGTTASLQ YMKNVFKEKY LLSEDTSGKF SVDKLKFDKL YKMLTEIYTE DNFVKFFKVL
361  NRKTYLNFDK AVFKINIVPK VNYTIYDGFN LRNTNLAANF NGQNTEINNM NFTKLKNFTG
421  LFEFYKLLCV RGIITSKTKS LDKGYNKALN DLCIKVNNWD LFFSPSEDNF TNDLNKGEEI
481  TSDTNIEAAE ENISLDLIQQ YYLTFNFDNE PENISIENLS SDIIGQLELM PNIERFPNGK
541  KYELDKYTMF HYLRAQEFEH GKSRIALTNS VNEALLNPSR VYTFFSSDYV KKVNKATEAA
601  MFLGWVEQLV YDFTDETSEV STTDKIADIT IIIPYIGPAL NIGNMLYKDD FVGALIFSGA
```

Fig. 1B.

```
 661  VILLEFIPEI  AIPVLGTFAL  VSYIANKVLT  VQTIDNALSK  RNEKWDEVYK  YIVTNWLAKV
 721  NTQIDLIRKK  MKEALENQAE  ATKAIINYQY  NQYTEEEKNN  INFNIDDLSS  KLNESINKAM
 781  ININKFLNQC  SVSYLMNSMI  PYGVKRLEDF  DASLKDALLK  YIYDNRGTLI  GQVDRLKDKV
                                                    Hc
 841  NNTLSTDIPF  QLSKYVDNQR  ILSTFTEYIK  NI|NTSILNL  RYESNHLIDL  SRYASKINIG
 901  SKVNFDPIDK  NQIQLFNLES  SKIEVILKNA  IVYNSMYENF  STSFWIRIPK  YFNSISLNNE
 961  YTIINCMENN  SGWKVSLNYG  EIIWDLQDTQ  EIKQRVVFKY  SQMINISDYI  NRWIFVTITN
1021  NRLNNSKIYI  NGRLIDQKPI  SNLGNIHASN  NIMFKLDGCR  DTHRYIWIKY  FNLFDKELNE
1081  KEIKDLYDNQ  SNSGILKDFW  GDYLQYDKPY  YMLNLYDPNK  YVDVNNVGIR  GYMYLKGPRG
1141  SVMTTNIYLN  SSLYRGTKFI  OKKYASGNKD  NIVRNNDRVY  INVVVKNKEY  RLATNASQVV
1201  VFKILSALEI  PDVGNLSQVV  VMKSKNDQGI  TNKCKMNLQD  NNGNDIGFIG  FHQFNNIAKL
1261  VASNWYNRQI  ERSSRTLGCS  WEFIPVDDGW  GERPL
```

NEUROTOXINS WITH ENHANCED TARGET SPECIFICITY

This application is a divisional and claims priority pursuant to 35 U.S.C. §120 to U.S. patent application Ser. No. 09/726,949, filed Nov. 29, 2000 now U.S. Pat. No. 7,273,722, which is hereby incorporated by reference in its entirety.

TECHNICAL FIELD

The invention is directed to modified neurotoxins which are deactivated in tissues where toxic activity is undesirable and neurotoxins that are activated at desired targets. More specifically, the invention concerns insertion of cleavage sites in non-critical regions of the toxins which are susceptible to protease activity in non-target tissues and to single chain forms which are activated by proteases in the target.

BACKGROUND ART

Structure and Function

Neurotoxins, such as those obtained from *Clostridium botulinum* and *Clostridium tetani*, are highly potent and specific poisons of neural cells. Both the single known tetanus toxin and the multiplicity of known *botulinum* toxins comprise, in their activated forms, two peptide acid chains coupled through a disulfide link: a light chain (LC) of about 50 KDa and a heavy chain (HC) of about 100 KDa. The toxins are synthesized in vivo as single chains, which are not toxic. However, the toxin becomes active when the single chain is nicked in a post-translational modification to form the separate LC and HC (linked by S-S).

The tetanus and *botulinum* toxins have lethal doses in humans of between 0.1 ng and 1 ng per kilogram of body weight. They function by inhibiting neurotransmitter release in affected neurons. The tetanus neurotoxin (TeNT) acts mainly in the central nervous system, while *botulinum* neurotoxin (BoNT) acts at the neuromuscular junction and other cholinergic synapses in the peripheral nervous system. Both types act by inhibiting acetylcholine release from the axon of the affected neuron into the synapse, resulting in paralysis. The effect of intoxication on the affected neuron is long-lasting and until recently has been thought to be irreversible.

Only one form of tetanus neurotoxin is known; seven different immunologically distinct forms of *botulinum* neurotoxins termed BoNT/A through BoNT/G are known. While all of these types are produced by isolates of *C. botulinum*, two other species, *C. baratii* and *C. butyricum* also produce toxins similar to /F and /E, respectively.

Regardless of type, the molecular mechanism of intoxication appears to be similar. First, the toxin binds to the presynaptic membrane of the target neuron through a specific interaction between the heavy chains (HC) and a cell surface receptor; the receptor is thought to be different for each type of *botulinum* toxin and for TeNT. The carboxyl terminus of the HC appears to be important for targeting of the toxin to the cell surface.

In the second step, the toxin crosses the plasma membrane of the poisoned cell, is engulfed by the cell through receptor-mediated endocytosis, and an endosome containing the toxin is formed. The toxin then escapes the endosome into the cytoplasm of the cell. The escape is thought to be mediated by a conformational change brought about by the acidic environment within the endosome which is effected by a proton pump that decreases intraendosomal pH. At a pH of about 5.5 or lower, the sequence at the amino terminus of the heavy chain triggers this conformational change. The conformation shift exposes hydrophobic residues which permits the toxin to embed itself in the endosome membrane and then translocate into the cytosol.

Once in the cytosol, reduction of the disulfide bond joining the HC and LC takes place. The entire toxic activity of *botulinum* and tetanus toxins is contained in the LC; which is a zinc ($Zn^{++}$) endopeptidase that selectively cleaves "SNARE" proteins essential for recognition and docking of neurotransmitter-containing vesicles with the cytoplasmic surface of the plasma membrane, and fusion of the vesicles with the plasma membrane.

The "SNARE" proteins are of several forms which have differential responses to the various forms of toxin. TeNT, BoNT/B BoNT/D, BoNT/F, and BoNT/G cause degradation of synaptobrevin (also called vesicle-associated membrane protein (VAMP)), a synaptosomal membrane protein. Most of the cytosolic domain of VAMP extending from the surface of the synaptic vesicle is removed as a result of any one of these cleavage events. Each toxin (except TeNT and BoNT/B) specifically cleaves a different bond.

BoNT/A and /E selectively cleave the plasma membrane-associated protein SNAP-25; this protein is predominantly bound to and present on the cytosolic surface of the plasma membrane. BoNT/C cleaves syntaxin, an integral protein having most of its mass exposed to the cytosol. Syntaxin interacts with the calcium channels at presynaptic terminal active zones.

Both TeNT and BoNT are taken up at the neuromuscular junction. BoNT remains within peripheral neurons, and blocks release of the neurotransmitter acetylcholine from these cells. TeNT enters vesicles that move in a retrograde manner along the axon to the soma, and is discharged into the intersynaptic space between motor neurons and the inhibitory neurons of the spinal cord. At this point, TeNT binds receptors of the inhibitory neurons, is again internalized, and the light chain enters the cytosol to block the release of the inhibitory neurotransmitters 4-aminobutyric acid (GABA) and glycine from these cells.

Pharmaceutical Applications

Dilute preparations of BoNT have been used since 1981 as therapeutic agents in the treatment of patients having various spastic conditions, including strabismus (misalignment of the eye), bephlarospasm (involuntary eyelid closure) and hemifacial spasm. See e.g., Borodic, et al., *Pharmacology and Histology of the Therapeutic Application of Botulinum Toxin* in *Therapy with Botulinum Toxin* 119-157 (Jankovic J. & Hallett, eds. 1994), hereby incorporated by reference herein. The toxin preparations are delivered specifically and locally to the site of the neurons to be effected. BoNT/A is the most potent of the BoNT's, and the best characterized. Intramuscular injection of dilute preparations of BoNT/A has also been used effectively to treat spastic conditions due to brain injury, spinal cord injury, stroke, multiple sclerosis and cerebral palsy. The extent of paralysis depends on both the dose and volume delivered to the target site.

Clearly, it is desirable to confine the activity of the administered toxin to the target site. A number of strategies have been adopted, including, besides direct injection, implantation of a capsule pump or administration of a slow release gel. However, the success of such attempts has been far from complete. Because of the diffusion of the toxin from the site of administration, systemic problems, such as difficulty in swallowing have occurred. The reality of these undesired effects has limited the level of dosage which can be administered. For example, subjects needing treatment in both arms or both legs generally cannot be administered the toxin in both affected limbs simultaneously due to the side effects. It would thus be desirable to provide a form of the toxins which inherently acts specifically at its target site. The present invention provides such modified forms.

DISCLOSURE OF THE INVENTION

The invention provides botulism and tetanus toxins, including variants and derivatives thereof, which contain protease target sites in non-critical regions such that specificity of toxicity with regard to a particular target tissue is conferred. In general, the toxins are active at the neuromuscular junction and thus, should be toxic in muscle tissue; they may also be active at sites in the central nervous system. Systemic spread occurs mainly through the bloodstream, and it would thus be desirable to inactivate the toxin as soon as any molecules enter the bloodstream. By suitable choice of cleavage sites, susceptible to blood or muscle proteases respectively, the toxins can be provided in a form which will be inactivated in blood, activated in muscle, or both. The cleavage site must be provided in a region of the toxin where its presence does not disrupt the activity of the toxin, but where cleavage results in activation or inactivation as the case may be.

Thus, in one aspect, the invention is directed to a modified botulism or tetanus toxin wherein the modification comprises the inclusion of a cleavage site in a domain that must remain intact for activity and where the cleavage site is susceptible to cleavage by a protease that is present in effective levels only in a tissue where toxic activity is undesirable and where the cleavage site itself does not inactivate the toxin. In another aspect, the invention is directed to a modified botulism or tetanus toxin wherein the modification comprises a target cleavage site for a protease such that an inactive form of the toxin is activated. In this case, the protease specific for the cleavage site would be present in an effective amount only in tissues where toxicity is desired.

Still another aspect, the invention is directed to toxins which are modified to contain cleavage sites of both types. Thus, such a toxin would be specifically activated in muscle but deactivated once it was transported into the blood stream.

In still another aspect, the invention is directed to recombinant materials encoding the modified toxins and to methods to produce them. The invention is also directed to methods to treat conditions benefited by neurotoxin activity which comprises administering the neurotoxins of the invention or administering expression systems for their localized production.

BRIEF DESCRIPTION OF THE DRAWINGS

FIG. 1 shows the amino acid sequence of botulism A toxin purified from *Clostridium botulinum* strain Hall A where residues 437-438 which are cleaved during post-translational modification are adopted from the conserved sequence obtained by DNA sequences of strains NCTC2916 and 62A.

MODES OF CARRYING OUT THE INVENTION

Figure 2:
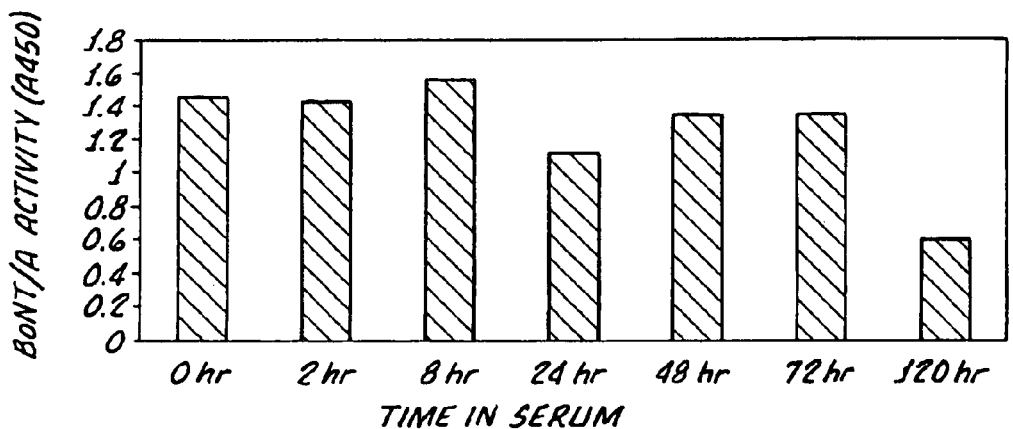
FIG. 2 is a graph showing the stability of botulism toxin A in human serum.

The botulism and tetanus toxins which are modified in order to obtain the desirable properties associated with the invention include, in addition to the naturally occurring forms, variants and derivatives of these forms. Such variants include, for example, chimeric forms of these toxins in which a portion of the heavy chain or light chain of BoNT/A is replaced by the corresponding region of BoNT/E or BoNT/G or tetanus toxin. Various combinations can be envisioned. The toxin may have a heavy chain from one native toxin combined with light chain of another. In addition, variants may contain, in regions that are irrelevant to activity, 1-5 substitutions, preferably by amino acids which are similar in character— i.e., conservative amino acid substitutions. The variants may also contain deletions of 1-5, preferably 1-3, more preferably 1-2 amino acids in regions where the activity is substantially unaffected. Derivatives of these toxins include forms that may be lipidated, PEGylated, phosphorylated, or otherwise derivatized by additional covalently bonded groups, including the N-terminal acylated and C-terminal amidated forms. Thus, the toxins which are modified according to the present invention may include a range of variants and derivatives of the naturally occurring toxins. As used and defined herein, the terms "botulism toxin" and "tetanus toxin" refer not only to the native toxins, but also to the variants and derivatives as described above.

The invention is directed to modified forms of botulism or tetanus toxin (including variants and derivatives as defined above) which contain protease cleavage sites. In the aspect wherein the cleavage site will result in inactivation of the toxin, the site must be present in a region wherein the presence of the cleavage site itself does not destroy toxic activity. By "does not destroy toxic activity" is meant that the toxic activity of the modified form is at least 10%, preferably 25%, more preferably 50%, more preferably 75% and most preferably at least 90% of the unmodified form. Forms wherein the toxic activity is equal to or exceeds that of the toxin itself are also included. Such non-critical regions can be determined experimentally by assessing the resulting toxicity of the modified toxin using standard toxicity assays such as that described by Zhou, L., et al., *Biochemistry* (1995) 34:15175-15181, which describes an in vitro assay for the ability of light chain to cleave recombinantly produced SNAP-25. Other suitable assays commonly practiced include simple injection into mice to evaluate lethality. These assays are described, for example, by Maisey, E. A., et al., *Eur J. Biochem.* (1988) 177:683-691.

However, rational decisions about the location of such sites can be based on the known conformation of the toxins. The crystal structure of botulism toxin type A is described, for example by Lacy, D. B., et al., *Nature Structural Biology* (1998) 5:898-902. Based on the crystal structure, and other data obtained with respect to botulism toxin type A, certain features are apparent as will be described below. Because of the similarity of all of the botulism toxins and tetanus toxins, the description that is set forth below in detail with respect to type A is applicable as well to the remaining toxin types and to tetanus toxins. The primary amino acid sequences are similar in all cases, and the functions and mechanisms of action are similar as well. Briefly, it appears that the light chain is globular, containing a number of exposed loops of minimal secondary structure; the heavy chain comprises two globular regions and a paired double helix. An extension of the light chain comprising a "belt" circumscribes a portion of the complex. Suitable regions for locating a protease target site, wherein cleavage results in inactivation would be found between the binding and transport domains, between the two globules of the binding domain of the heavy chain, in the non-catalytic regions of the light chain, and in the belt region.

Other features of the protein are also known. Recent studies of the BoNT/A light chain have revealed certain features important for the activity and specificity of the toxin towards its target substrate, SNAP-25. Thus, studies by Zhou, et al., *Biochemistry* 34:15175-15181 (1995) have indicated that when the light chain amino acid residue His$_{227}$ is substituted with tyrosine, the resulting polypeptide is unable to cleave SNAP-25; Kurazono, et al., *J. Biol. Chem.* 14721-14729 (1992) performed studies in the presynaptic cholinergic neurons of the buccal ganglia of *Aplysia californica* using recombinant BoNT/A light chain that indicated that the removal of 8 N-terminal or 32 C-terminal residues did not abolish toxicity, but that removal of 10 N-terminal or 57 C-terminal residues abolished toxicity in this system. Most recently, the crystal structure of the entire BoNT/A holotoxin has been solved; the active site is indicated as involving the participation of His$_{222}$, Glu$_{223}$, His$_{226}$, Glu$_{261}$ and Tyr$_{365}$. Lacy, et al., supra. (These residues correspond to His$_{223}$, Glu$_{224}$, His$_{227}$, Glu$_{262}$ and Tyr$_{366}$ of the BoNT/A L chain of Kurazono et al., supra.) Interestingly, an alignment of BoNT/A through E and TeNT light chains reveals that every such chain invariably has these residues in positions analogous to BoNT/A. Kurazono, et al., supra.

The catalytic domain of BoNT/A is very specific for the C-terminus of SNAP-25 and appears to require a minimum of 17 SNAP-25 amino acids for cleavage to occur. The catalytic site resembles a pocket; when the light chain is linked to the heavy chain via the disulfide bond between Cys$_{429}$ and Cys$_{453}$, the translocation domain of the heavy chain appears to block access to the catalytic pocket until the light chain gains entry to the cytosol. When the disulfide bond is then reduced, the catalytic pocket is "opened" and the light chain is fully active. As described above, VAMP and syntaxin are cleaved by BoNT/B, D, F, G and TeNT, and BoNT/C$_1$, respectively, while SNAP-25 is cleaved by BoNT/A and E.

While the presence of the cleavage site itself must permit the toxic activity to be retained, actual cleavage at the site must result in inactivation. By inactivation in this context is meant that the toxin retains only 50% of the toxicity, preferably only 25% of the toxicity, more preferably only 10% of the toxicity, more preferably only 1% of the toxicity of the uncleaved form. Thus, while the position of the site should be in a non-critical region with respect to the site itself, cleavage at that site must have a substantial effect.

For the design of a botulism toxin which can be inactivated by blood, protease sites which are recognized by proteases relatively uniquely found in the bloodstream are desirable. Among these proteases are those set forth below in Table 1 which also describes their recognition sites.

TABLE 1

Proteases Present in Blood

| Blood protease | Substrate Specificity |
|---|---|
| Thrombin | P4-P3-P-R/K*P1'-P2' P3/P4 hydrophobic; P1'/P2' non-acidic P2-R/K*P1' P2 or P1' are G |
| Coagulation Factor Xa | I-E-G-R* (SEQ ID NO: 13) I-D-G-R* (SEQ ID NO: 14) |
| Coagulation Factor XIa | R* |
| Coagulation Factor XIIa | R* |
| Coagulation Factor IXa | R* |
| Coagulation Factor VIIa | R/K* |
| Kallikrein | R/K* |
| Protein C | R* |
| MBP-associated serine protease | R* |
| Oxytocinase | N-terminal C* |
| Lysine carboxypeptidase | C-terminal R/K* |

*indicates the peptide bond this protease will cleave.

As is clear, coagulation factors XIa, XIIa, IXa and VIIa as well as kallikrein, protein C, MBP-associated serine protease, oxytocinase and lysine carboxypeptidase have relatively non-specific target sites, while coagulation factors Xa and thrombin provide the opportunity for more specificity.

In designing a thrombin or coagulation factor Xa site into a botulism toxin, the location of the inserted site is, as described above, such that the presence of the site will not interfere with activity of the toxin, but cleavage at the site will destroy or vastly inhibit the activity of the toxin. In general, the early steps of the action can be targeted by placing the site into the receptor binding region or the internalization region in the heavy chain, but away from the functional domains within these regions. Insertion sites in the heavy chain receptor binding domain should be away from receptor binding grooves and in all cases the sites should be selected so as to be on the surface of the protein so that blood proteases can freely access them.

Table 2 indicates some examples of site modifications for cleavage by thrombin in the botulism toxin A amino acid sequence set forth in FIG. 1. In the table, the underline indicates a thrombin recognition site, the residues in bold are the additional amino acids; residues which were present in the native sequence but are eliminated when the site is inserted are in parentheses. An asterisk indicates the peptide bond the thrombin will cleave.

TABLE 2

Thrombin Site Insertion

| Amino acid residue | Location | Example of thrombin site insertion |
|---|---|---|
| 930-AIVYNS-935 (SEQ ID NO: 2) | H$_C$ | -A-I-R*G(VY)-N-S- (SEQ ID NO: 3) -A-I-P-R*(VY)-N-S- (SEQ ID NO: 4) -A-I-P-R*V-Y-N-S- (SEQ ID NO: 5) |
| 1060-RDTH-1063 (SEQ ID NO: 6) | H$_C$ | -G-R*D-T-H- (SEQ ID NO: 7) |
| 1136-KGPRGSVMT-1144 (SEQ ID NO: 8) | H$_C$ | -I(K)-G-P-R*G-S-V-M-T- (SEQ ID NO: 9) |
| 1165-ASGNKDN-1171 (SEQ ID NO: 10) | H$_C$ | -A-S-G-G(N)-K*D-N- (SEQ ID NO: 11) -A-L(S)-G-P(N)-K*G(D)-N- (SEQ ID NO: 12) |

The locations of the sites proposed are also set forth in FIG. 1.

Thus, for the inactivating cleavage, the protease should be one present in high levels in blood. A suitable protease in this regard is thrombin, which, as shown below, occurs in blood in levels sufficient to deactivate the modified form of the toxins herein. By "effective" level of the protease is meant a concentration which is able to inactivate at least 50%, preferably 75%, more preferably 90% or greater of the toxin which enters the bloodstream at clinically suitable levels of dosage. In general, the dosage levels for botulism toxins are on the order of nanogram levels of concentration and thus are not expected to require higher concentrations of protease.

With respect to forms of toxins which are selectively activated by muscle, preferably these comprise the single chain forms of the toxin precursor. Such forms, which are resistant to proteolytic activity by the *Clostridium* itself, have been designed for recombinant production in other organisms such as *E. coli*. Indeed, in some cases, the *Clostridium* produces mostly the uncleaved single chain form.

Single chain forms with a proteolytic site in the interchain loop region for cleavage by enzymes applied in vitro is described in application No. 60/150,710 filed 25 Oct. 1999, and incorporated by reference. As described in this application, a single chain form of tetanus or botulism toxin is constructed by ligating the nucleotide sequences encoding light and heavy chain through a linker region corresponding, for example, to residue 437-448 of FIG. 1. In the case of the present invention, this linker region is provided with a target site for a protease which is specifically present at sufficient concentrations in muscle to effect cleavage at this site.

As the production of the single chain form involves genetic manipulation, (as does the construction of the form which is subject to inactivation in blood) mixing and matching of various regions of the seven botulism toxins and the tetanus toxin is well within the skill of the artisan. Thus, a botulism A light chain might be used in combination with botulism toxin B heavy chain or with a tetanus heavy chain transmembrane region and a botulism G receptor recognition region. The particular toxin exemplified as a single chain product in the above-referenced provisional application is a single chain tetanus toxin, but clearly other single chain toxins with appropriate protease sites could be readily engineered. Thus, in the present invention, the nature of the protease cleavage site will be altered so as to be susceptible to muscle proteases.

The substrate neurotoxins which can be modified according to the method of the invention are those natively occurring as described in the Background section above, or can be themselves modified such as those described in PCT publications WO95/32738, WO96/33273, WO98/07864 and WO99/17806, all incorporated herein by reference. As stated above, the selectively activated and inactivated toxins of the invention have the further advantage that heavy chain and light chain components of the neurotoxins can be readily mixed and matched, and prepared as chimeras.

The following examples are intended to illustrate but not to limit the invention.

EXAMPLE 1

Thrombin Activity in Blood

The substrate for assay of thrombin proteolytic activity is the GST-SNAP-25 (a.a.128-197) fusion protein with a thrombin cleavage site inserted between the two proteins. The substrate was added in a solution containing 10 µg/1.55 µl to 8.45 µl of PBS or blood preparations to make the final volume at 10 µl. The mixtures were incubated at 37° C. One µl (containing 1 µg of the substrate) used in each treatment was mixed with 1 µl of 2× sample buffer with DTT and boiled for 5 minutes before loading to 18% SDS-PAGE gel. The gel was then blotted and probed with Ab 197, which recognizes the C-terminal end of the cleaved or uncleaved SNAP-25$_{128\text{-}197}$.

Results showed that the substrate was cleaved by serum and at a much lower level, by whole blood. No cleavage product was detected by incubating with plasma. The lack of thrombin activity in the plasma suggests the majority of the enzyme is probably still in its proenzyme form (prothrombin). Prothrombin is activated to thrombin as a result of a cascade of proteolytic enzymes that initiate blood coagulation, and thus thrombin is present in the serum because the clotting has been triggered, but not in plasma where the clotting was prohibited by adding citrate. the trace amount of thrombin cleavage product seen in the sample incubated with citrated whole blood indicates that a low level of clotting pathway activation has occurred.

As typically these toxins are injected at very low (nanogram) levels, the thrombin levels in blood, even at the low levels of activation shown may be sufficient to effect at least sufficient cleavage substantially to inactivate the toxin. In addition, the trauma caused by injection of the toxin may trigger activation of prothrombin to elevate these levels.

EXAMPLE 2

Stability of Native BoNT/A with Respect to Proteases

To test the stability of unmodified BoNT/A in human serum, BoNT/A was added at 10 µg/ml of human serum and incubated for the time specified. The activity of the toxin was measured by the absorbance at 450 nm in the SNAP-25 assay described in co-pending application Ser. No. 09/164,692, filed 25 Aug. 2000, claiming priority to provisional application Ser. No. 60/150,710 filed 25 Aug. 1999, both incorporated herein by reference. The absorbance value was compared at the dilution of 1000 pg toxin per ml. As shown in FIG. 2, BoNT/A is fairly stable in human serum for up to 4 days and still retained 50% of the activity after 5 days in the serum. Similar results were found when incubating pure BoNT/A or complex with whole blood or plasma and the toxins were stable for up to 48 hours tested. These results suggest BoNT/A is stable in the blood without immediate breakdown by plasma protease and therefore will potentially circulate to other muscles and organs and cause a systemic effect unless inactivated by the invention method.

Figure 3:
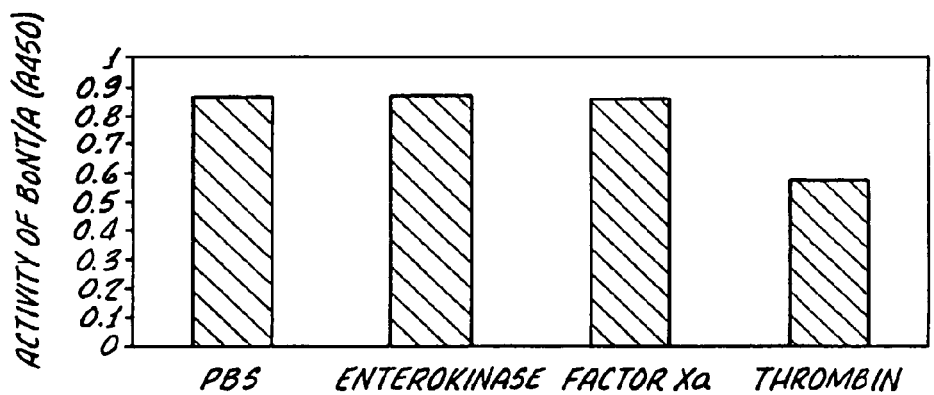
FIG. 3 is a graph showing the resistance of botulism toxin A to various proteases.

The resistance of BoNT/A to various proteases. BoNT/A was incubated overnight with excess purified restricted proteases at room temperature and then the activity was analyzed by the SNAP-25 assay such as that referenced above. Factor Xa and thrombin are plasma proteases; enterokinase is present in the duodenal secretions into the GI tract. Activities are compared at 100 pg/ml dilution of each toxin reaction. The results are shown in FIG. 3. The toxin is resistant to these proteases. Although the toxin incubated with thrombin lost ⅓ of its activity, it may not be very sensitive to thrombin degradation since an excess of enzyme was used for a long period of time. SDS-PAGE gel analysis of these treated toxins showed no cleavage.

The invention claimed is:

1. A nucleic acid molecule which comprises a nucleotide sequence encoding a modified *botulinum* A neurotoxin comprising:
 a) a binding domain comprising a first heavy chain portion able to interact with a surface receptor present in a target cell, wherein said first heavy chain portion comprises a mammalian blood protease cleavage site, said mammalian blood protease cleavage site comprising a modification in one or more regions selected from the group consisting of amino acids 930-935 of SEQ ID NO: 1, amino acids 1060-1063 of SEQ ID NO: 1, amino acids 1136-1144 of SEQ ID NO: 1 and amino acids 1165-1171 of SEQ ID NO: 1;
 b) a translocation domain comprising a second heavy chain portion able to mediate the escape of a light chain portion of said neurotoxin from an endosome to the cytoplasm of said target cell; and
 c) an enzymatic domain comprising said light chain portion able to cleave a SNARE-protein present in said target cell;
  wherein said modified *botulinum* A neurotoxin is able to interact with a surface receptor of said target cell, able to mediate endosomal escape into the cytoplasm of said target cell and able to cleave a SNARE protein present in said target cell; and
  whereupon said modified *botulinum* A neurotoxin's ability to interact with a surface receptor of said target cell is inactivated upon cleavage of said mammalian blood protease cleavage site.

2. A nucleic acid molecule which comprises a nucleotide sequence encoding a modified *botulinum* A neurotoxin comprising:
 a) a binding domain comprising a first heavy chain portion able to interact with a surface receptor present in a target cell, wherein said first heavy chain portion comprises a mammalian blood protease cleavage site, said mammalian blood protease cleavage site comprising a modification in one or more regions selected from the group consisting of amino acids 930-935 of SEQ ID NO: 1, amino acids 1060-1063 of SEQ ID NO: 1, amino acids 1136-1145 of SEQ ID NO: 1 and amino acids 1165-1171 of SEQ ID NO: 1;
- b) a translocation domain comprising a second heavy chain portion able to mediate the escape of a light chain portion of said neurotoxin from an endosome to the cytoplasm of said target cell; and
- c) an enzymatic domain comprising said light chain portion able to cleave a SNARE-protein present in said target cell, wherein said light chain portion comprises a mammalian muscle protease cleavage site, said mammalian muscle protease cleavage site comprising a modification in amino acids 430-452 of SEQ ID NO: 1;
  - wherein said modified botulinum A neurotoxin is able to interact with a surface receptor of said target cell, able to mediate endosomal escape into the cytoplasm of said target cell and able to cleave a SNARE protein present in said target cell; and
  - whereupon said modified botulinum A neurotoxin's ability to interact with a surface receptor of said target cell is inactivated upon cleavage of said mammalian blood protease cleavage site; and
  - whereupon said modified botulinum A neurotoxin's ability to cleave a SNARE protein present in a target cell is activated upon cleavage of said mammalian muscle protease cleavage site.

3. The nucleic acid molecule according to either claim 1 or claim 2, wherein said mammalian blood protease cleavage site is cleaved by a mammalian blood protease selected from the group consisting of Thrombin, Coagulation Factor VIIa, Coagulation Factor IXa, Coagulation Factor Xa, Coagulation Factor XIa, Coagulation Factor XIIa, Kallikrein, Protein C and MBP-associated serine protease.

4. The nucleic acid molecule according to either claim 1 or claim 2, wherein said modification of amino acids 930-935 of SEQ ID NO: 1 is selected from the group consisting of SEQ ID NO: 3, SEQ ID NO: 4 and SEQ ID NO: 5.

5. The nucleic acid molecule according to either claim 1 or claim 2, wherein said modification of amino acids 1060-1063 of SEQ ID NO: 1 is SEQ ID NO: 7.

6. The nucleic acid molecule according to either claim 1 or claim 2, wherein said modification of amino acids 1136-1145 of SEQ ID NO: 1 is SEQ ID NO: 9.

7. The nucleic acid molecule according to either claim 1 or claim 2, wherein said modification of amino acids 1165-1171 of SEQ ID NO: 1 is selected from the group consisting of SEQ ID NO: 11 and SEQ ID NO: 12.

8. An expression system which comprises the nucleotide sequence of according to claim 1 operably linked to sequences for effecting its expression.

9. A recombinant host cell modified to contain the expression system of claim 8.

10. A method to produce a modified botulinum A neurotoxin, the method comprising the steps of culturing the host cell of claim 9 under conditions wherein said modified botulinum A neurotoxin is produced and optionally recovering the modified botulinum A neurotoxin from the culture.

11. A nucleic acid molecule which comprises a nucleotide sequence encoding a modified botulinum A neurotoxin comprising a blood protease cleavage site, wherein said blood protease cleavage site comprises a modification in one or more regions selected from the group consisting of amino acids 930-935 of SEQ ID NO: 1, amino acids 1060-1063 of SEQ ID NO: 1, amino acids 1136-1145 of SEQ ID NO: 1 and amino acids 1165-1171 of SEQ ID NO: 1.

12. A nucleic acid molecule which comprises a nucleotide sequence encoding a modified botulinum A neurotoxin comprising a blood protease cleavage site and a muscle protease cleavage site,
  - wherein said blood protease cleavage site comprises a modification in one or more regions selected from the group consisting of amino acids 930-935 of SEQ ID NO: 1, amino acids 1060-1063 of SEQ ID NO: 1, amino acids 1136-1145 of SEQ ID NO: 1 and amino acids 1165-1171 of SEQ ID NO: 1; and
  - wherein said muscle protease cleavage site comprises a modification in amino acids 430-452 of SEQ ID NO: 1.

13. The nucleic acid molecule according to either claim 11 or claim 12, wherein said mammalian blood protease cleavage site is cleaved by a mammalian blood protease selected from the group consisting of Thrombin, Coagulation Factor VIIa, Coagulation Factor IXa, Coagulation Factor Xa, Coagulation Factor XIa, Coagulation Factor XIIa, Kallikrein, Protein C and MBP-associated serine protease.

14. The nucleic acid molecule according to either claim 11 or claim 12, wherein said modification of amino acids 930-935 of SEQ ID NO: 1 is selected from the group consisting of SEQ ID NO: 3, SEQ ID NO: 4 and SEQ ID NO: 5.

15. The nucleic acid molecule according to either claim 11 or claim 12, wherein said modification of amino acids 1060-1063 of SEQ ID NO: 1 is SEQ ID NO: 7.

16. The nucleic acid molecule according to either claim 11 or claim 12, wherein said modification of amino acids 1136-1145 of SEQ ID NO: 1 is SEQ ID NO: 9.

17. The nucleic acid molecule according to either claim 11 or claim 12, wherein said modification of amino acids 1165-1171 of SEQ ID NO: 1 is selected from the group consisting of SEQ ID NO: 11 and SEQ ID NO: 12.

18. An expression system which comprises the nucleotide sequence of according to claim 11 operably linked to sequences for effecting its expression.

19. A recombinant host cell modified to contain the expression system of claim 18.

20. A method to produce a modified botulinum A neurotoxin, the method comprising the steps of culturing the host cell of claim 19 under conditions wherein said modified botulinum A neurotoxin is produced and optionally recovering the modified botulinum A neurotoxin from the culture.

* * * * *

UNITED STATES PATENT AND TRADEMARK OFFICE
CERTIFICATE OF CORRECTION

PATENT NO. : 7,456,272 B2 Page 1 of 1
APPLICATION NO. : 11/832901
DATED : November 25, 2008
INVENTOR(S) : Lin et al.

It is certified that error appears in the above-identified patent and that said Letters Patent is hereby corrected as shown below:

On the Title page, Item (56), under "U.S. Patent Documents", in column 1, line 29, delete "Donvan" and insert -- Donovan --, therefor.

In column 1, line 3, below "SPECIFICITY"
insert -- CROSS-REFERENCE TO RELATED APPLICATIONS --.

In column 2, line 45, delete "bephlarospasm" and insert -- blepharospasm --, therefor.

Signed and Sealed this

Third Day of February, 2009

JOHN DOLL
*Acting Director of the United States Patent and Trademark Office*

SEQUENCE LISTING

<160> NUMBER OF SEQ ID NOS: 14

<210> SEQ ID NO 1
<211> LENGTH: 1295
<212> TYPE: PRT
<213> ORGANISM: Clostridium botulinum Serotype A

<400> SEQUENCE: 1

```
Pro Phe Val Asn Lys Gln Phe Asn Tyr Lys Asp Pro Val Asn Gly Val
 1               5                  10                  15

Asp Ile Ala Tyr Ile Lys Ile Pro Asn Val Gly Gln Met Gln Pro Val
            20                  25                  30

Lys Ala Phe Lys Ile His Asn Lys Ile Trp Val Ile Pro Glu Arg Asp
        35                  40                  45

Thr Phe Thr Asn Pro Glu Glu Gly Asp Leu Asn Pro Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Asp Thr Glu Leu Lys Val
        115                 120                 125

Ile Asp Thr Asn Cys Ile Asn Val Ile Gln Pro Asp Gly Ser Tyr Arg
    130                 135                 140

Ser Glu Glu Leu Asn Leu Val Ile Ile Gly Pro Ser Ala Asp Ile Ile
145                 150                 155                 160

Gln Phe Glu Cys Lys Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Glu Leu
    210                 215                 220

Ile His Ala Gly His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
        275                 280                 285

Phe Lys Asp Ile Ala Ser Thr Leu Asn Lys Ala Lys Ser Ile Val Gly
    290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
            340                 345                 350

Phe Val Lys Phe Phe Lys Val Leu Asn Arg Lys Thr Tyr Leu Asn Phe
```

-continued

```
                355                 360                 365
Asp Lys Ala Val Phe Lys Ile Asn Ile Val Pro Lys Val Asn Tyr Thr
    370                 375                 380
Ile Tyr Asp Gly Phe Asn Leu Arg Asn Thr Asn Leu Ala Ala Asn Phe
385                 390                 395                 400
Asn Gly Gln Asn Thr Glu Ile Asn Asn Met Asn Phe Thr Lys Leu Lys
                405                 410                 415
Asn Phe Thr Gly Leu Phe Glu Phe Tyr Lys Leu Leu Cys Val Arg Gly
                420                 425                 430
Ile Ile Thr Ser Lys Thr Lys Ser Leu Asp Lys Gly Tyr Asn Lys Ala
                435                 440                 445
Leu Asn Asp Leu Cys Ile Lys Val Asn Asn Trp Asp Leu Phe Phe Ser
    450                 455                 460
Pro Ser Glu Asp Asn Phe Thr Asn Asp Leu Asn Lys Gly Glu Glu Ile
465                 470                 475                 480
Thr Ser Asp Thr Asn Ile Glu Ala Ala Glu Asn Ile Ser Leu Asp
                485                 490                 495
Leu Ile Gln Gln Tyr Tyr Leu Thr Phe Asn Phe Asp Asn Glu Pro Glu
                500                 505                 510
Asn Ile Ser Ile Glu Asn Leu Ser Ser Asp Ile Ile Gly Gln Leu Glu
                515                 520                 525
Leu Met Pro Asn Ile Glu Arg Phe Pro Asn Gly Lys Lys Tyr Glu Leu
    530                 535                 540
Asp Lys Tyr Thr Met Phe His Tyr Leu Arg Ala Gln Glu Phe Glu His
545                 550                 555                 560
Gly Lys Ser Arg Ile Ala Leu Thr Asn Ser Val Asn Glu Ala Leu Leu
                565                 570                 575
Asn Pro Ser Arg Val Tyr Thr Phe Phe Ser Ser Asp Tyr Val Lys Lys
                580                 585                 590
Val Asn Lys Ala Thr Glu Ala Ala Met Phe Leu Gly Trp Val Glu Gln
                595                 600                 605
Leu Val Tyr Asp Phe Thr Asp Glu Thr Ser Glu Val Ser Thr Thr Asp
    610                 615                 620
Lys Ile Ala Asp Ile Thr Ile Ile Pro Tyr Ile Gly Pro Ala Leu
625                 630                 635                 640
Asn Ile Gly Asn Met Leu Tyr Lys Asp Asp Phe Val Gly Ala Leu Ile
                645                 650                 655
Phe Ser Gly Ala Val Ile Leu Leu Glu Phe Ile Pro Glu Ile Ala Ile
                660                 665                 670
Pro Val Leu Gly Thr Phe Ala Leu Val Ser Tyr Ile Ala Asn Lys Val
                675                 680                 685
Leu Thr Val Gln Thr Ile Asp Asn Ala Leu Ser Lys Arg Asn Glu Lys
    690                 695                 700
Trp Asp Glu Val Tyr Lys Tyr Ile Val Thr Asn Trp Leu Ala Lys Val
705                 710                 715                 720
Asn Thr Gln Ile Asp Leu Ile Arg Lys Lys Met Lys Glu Ala Leu Glu
                725                 730                 735
Asn Gln Ala Glu Ala Thr Lys Ala Ile Ile Asn Tyr Gln Tyr Asn Gln
                740                 745                 750
Tyr Thr Glu Glu Glu Lys Asn Asn Ile Asn Phe Asn Ile Asp Asp Leu
                755                 760                 765
Ser Ser Lys Leu Asn Glu Ser Ile Asn Lys Ala Met Ile Asn Ile Asn
    770                 775                 780
```

-continued

```
Lys Phe Leu Asn Gln Cys Ser Val Ser Tyr Leu Met Asn Ser Met Ile
785                 790                 795                 800

Pro Tyr Gly Val Lys Arg Leu Glu Asp Phe Asp Ala Ser Leu Lys Asp
                805                 810                 815

Ala Leu Leu Lys Tyr Ile Tyr Asp Asn Arg Gly Thr Leu Ile Gly Gln
                820                 825                 830

Val Asp Arg Leu Lys Asp Lys Val Asn Thr Leu Ser Thr Asp Ile
                835                 840                 845

Pro Phe Gln Leu Ser Lys Tyr Val Asp Asn Gln Arg Leu Leu Ser Thr
850                 855                 860

Phe Thr Glu Tyr Ile Lys Asn Ile Ile Asn Thr Ser Ile Leu Asn Leu
865                 870                 875                 880

Arg Tyr Glu Ser Asn His Leu Ile Asp Leu Ser Arg Tyr Ala Ser Lys
                885                 890                 895

Ile Asn Ile Gly Ser Lys Val Asn Phe Asp Pro Ile Asp Lys Asn Gln
                900                 905                 910

Ile Gln Leu Phe Asn Leu Glu Ser Ser Lys Ile Glu Val Ile Leu Lys
                915                 920                 925

Asn Ala Ile Val Tyr Asn Ser Met Tyr Glu Asn Phe Ser Thr Ser Phe
930                 935                 940

Trp Ile Arg Ile Pro Lys Tyr Phe Asn Ser Ile Ser Leu Asn Asn Glu
945                 950                 955                 960

Tyr Thr Ile Ile Asn Cys Met Glu Asn Asn Ser Gly Trp Lys Val Ser
                965                 970                 975

Leu Asn Tyr Gly Glu Ile Ile Trp Thr Leu Gln Asp Thr Gln Glu Ile
                980                 985                 990

Lys Gln Arg Val Val Phe Lys Tyr Ser Gln Met Ile Asn Ile Ser Asp
                995                 1000                1005

Tyr Ile Asn Arg Trp Ile Phe Val Thr Ile Thr Asn Asn Arg Leu Asn
                1010                1015                1020

Asn Ser Lys Ile Tyr Ile Asn Gly Arg Leu Ile Asp Gln Lys Pro Ile
1025                1030                1035                1040

Ser Asn Leu Gly Asn Ile His Ala Ser Asn Asn Ile Met Phe Lys Leu
                1045                1050                1055

Asp Gly Cys Arg Asp Thr His Arg Tyr Ile Trp Ile Lys Tyr Phe Asn
                1060                1065                1070

Leu Phe Asp Lys Glu Leu Asn Glu Lys Glu Ile Lys Asp Leu Tyr Asp
                1075                1080                1085

Asn Gln Ser Asn Ser Gly Ile Leu Lys Asp Phe Trp Gly Asp Tyr Leu
                1090                1095                1100

Gln Tyr Asp Lys Pro Tyr Tyr Met Leu Asn Leu Tyr Asp Pro Asn Lys
1105                1110                1115                1120

Tyr Val Asp Val Asn Asn Val Gly Ile Arg Gly Tyr Met Tyr Leu Lys
                1125                1130                1135

Gly Pro Arg Gly Ser Val Met Thr Thr Asn Ile Tyr Leu Asn Ser Ser
                1140                1145                1150

Leu Tyr Arg Gly Thr Lys Phe Ile Ile Lys Lys Tyr Ala Ser Gly Asn
                1155                1160                1165

Lys Asp Asn Ile Val Arg Asn Asn Asp Arg Val Tyr Ile Asn Val Val
                1170                1175                1180

Val Lys Asn Lys Glu Tyr Arg Leu Ala Thr Asn Ala Ser Gln Ala Gly
1185                1190                1195                1200
```

```
Val Glu Lys Ile Leu Ser Ala Leu Glu Ile Pro Asp Val Gly Asn Leu
            1205                1210                1215

Ser Gln Val Val Val Met Lys Ser Lys Asn Asp Gln Gly Ile Thr Asn
        1220                1225                1230

Lys Cys Lys Met Asn Leu Gln Asp Asn Gly Asn Asp Ile Gly Phe
        1235                1240                1245

Ile Gly Phe His Gln Phe Asn Asn Ile Ala Lys Leu Val Ala Ser Asn
    1250                1255                1260

Trp Tyr Asn Arg Gln Ile Glu Arg Ser Ser Arg Thr Leu Gly Cys Ser
1265                1270                1275                1280

Trp Glu Phe Ile Pro Val Asp Asp Gly Trp Gly Glu Arg Pro Leu
            1285                1290                1295

<210> SEQ ID NO 2
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Amino acids 930 to 935 of SEQ ID NO: 1

<400> SEQUENCE: 2

Ala Ile Val Tyr Asn Ser
1               5

<210> SEQ ID NO 3
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin recognition site

<400> SEQUENCE: 3

Ala Ile Arg Gly Asn Ser
1               5

<210> SEQ ID NO 4
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin recognition site

<400> SEQUENCE: 4

Ala Ile Pro Arg Asn Ser
1               5

<210> SEQ ID NO 5
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: Thrombin recognition site

<400> SEQUENCE: 5

Ala Ile Pro Arg Val Tyr Asn Ser
1               5
```

```
<210> SEQ ID NO 6
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Amino acids 1060 to 1063 of SEQ ID NO: 1

<400> SEQUENCE: 6

Arg Asp Thr His
 1

<210> SEQ ID NO 7
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Thrombin recognition site

<400> SEQUENCE: 7

Gly Arg Asp Thr His
 1               5

<210> SEQ ID NO 8
<211> LENGTH: 9
<212> TYPE: PRT
<213> ORGANISM: Artificial Sequence
<220> FEATURE:
<221> NAME/KEY: SITE
<222> LOCATION: (1)...(9)
<223> OTHER INFORMATION: Amino acids 1136 to 1145 of SEQ ID NO: 1

<400> SEQUENCE: 8

Lys Gly Pro Arg Gly Ser Val Met Thr
 1               5

<210> SEQ ID NO 9
<211> LENGTH: 9
<212> TYPE: PRT
<213> ORGANISM: Artificial Sequence
<220> FEATURE:
<221> NAME/KEY: SITE
<222> LOCATION: (1)...(9)
<223> OTHER INFORMATION: Thrombin recognition site

<400> SEQUENCE: 9

Ile Gly Pro Arg Gly Ser Val Met Thr
 1               5

<210> SEQ ID NO 10
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Amino acids 1165 to 1171 of SEQ ID NO: 1

<400> SEQUENCE: 10

Ala Ser Gly Asn Lys Asp Asn
 1               5

<210> SEQ ID NO 11
<211> LENGTH: 7
<212> TYPE: PRT
<213> ORGANISM: Artificial Sequence
```

-continued

```
<220> FEATURE:
<221> NAME/KEY: SITE
<222> LOCATION: (1)...(7)
<223> OTHER INFORMATION: Thrombin recognition site

<400> SEQUENCE: 11

Ala Ser Gly Gly Lys Asp Asn
 1               5

<210> SEQ ID NO 12
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Thrombin recognition site

<400> SEQUENCE: 12

Ala Leu Gly Pro Lys Gly Asn
 1               5

<210> SEQ ID NO 13
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Coagulation Factor Xa site

<400> SEQUENCE: 13

Ile Glu Gly Arg
 1

<210> SEQ ID NO 14
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Coagulation Factor Xa site

<400> SEQUENCE: 14

Ile Asp Gly Arg
 1
```